(12) United States Patent  
Briand

(10) Patent No.: US 11,684,517 B2  
(45) Date of Patent: Jun. 27, 2023

(54) MEDICAL DEVICE FOR IMPROVING ENVIRONMENTAL PERCEPTION FOR BLIND OR VISUALLY-IMPAIRED USERS

(71) Applicant: Pierre Briand, Vélizy-Villacoublay (FR)

(72) Inventor: Pierre Briand, Vélizy-Villacoublay (FR)

( * ) Notice: Subject to any disclaimer, the term of this patent is extended or adjusted under 35 U.S.C. 154(b) by 0 days.

(21) Appl. No.: 17/414,704

(22) PCT Filed: Nov. 15, 2019

(86) PCT No.: PCT/FR2019/052721  
§ 371 (c)(1),  
(2) Date: Jun. 16, 2021

(87) PCT Pub. No.: WO2020/128173  
PCT Pub. Date: Jun. 25, 2020

(65) Prior Publication Data  
US 2022/0062053 A1 Mar. 3, 2022

(30) Foreign Application Priority Data  
Dec. 17, 2018 (FR) ...................... 18 73115

(51) Int. Cl.  
*A61F 9/08* (2006.01)  
*G06F 3/01* (2006.01)  
*H04N 7/18* (2006.01)

(52) U.S. Cl.  
CPC ............... *A61F 9/08* (2013.01); *G06F 3/013* (2013.01); *H04N 7/18* (2013.01)

(58) Field of Classification Search  
None  
See application file for complete search history.

(56) References Cited

U.S. PATENT DOCUMENTS

2006/0235263 A1* 10/2006 Jacobson ............... A61F 2/02  
600/31  
2007/0016425 A1* 1/2007 Ward .................. G09B 21/003  
704/271  
(Continued)

FOREIGN PATENT DOCUMENTS

WO 2013/018090 A1 2/2013

OTHER PUBLICATIONS

International Search Report (with English translation) and Written Opinion (with Machine translation) dated May 28, 2020 in corresponding International Application No. PCT/FR2019/052721; 13 pages.

*Primary Examiner* — Talha M Nawaz  
(74) *Attorney, Agent, or Firm* — Maier & Maier, PLLC

(57) ABSTRACT

A device for improving environmental perception for blind or visually impaired users, including a set of mechanical actuators intended to be in contact with the skin of a user, at least one digital camera designed to acquire a current digital image of an environment facing the user, a processing circuit connected to the camera for receiving pixel signals from the acquired digital image and converting at least one portion of the pixel signals into control signals, each of which powers a mechanical actuator of the set of actuators, an eye-tracking module for tracking each eye of the user to identify a gaze direction of the user. The processing circuit then selects, in the environment filmed by the camera, an area of acquired current image which is a function of the gaze direction and converts the pixel signals of said area into control signals, each of which powers an actuator of the set to stimulate the user's skin.

9 Claims, 4 Drawing Sheets

(56) References Cited

U.S. PATENT DOCUMENTS

| | | | |
|---|---|---|---|
| 2007/0041600 A1 | 2/2007 | Zachman | |
| 2013/0093852 A1* | 4/2013 | Ye | A61H 3/068 |
| | | | 348/46 |
| 2014/0184384 A1* | 7/2014 | Zhu | G09B 21/003 |
| | | | 340/4.12 |
| 2015/0366504 A1* | 12/2015 | Connor | A61B 5/6804 |
| | | | 600/301 |
| 2016/0030764 A1* | 2/2016 | Entis | A61N 7/00 |
| | | | 601/2 |
| 2016/0321955 A1* | 11/2016 | Zhu | G09B 21/007 |
| 2017/0068119 A1* | 3/2017 | Antaki | G06F 3/005 |
| 2018/0249151 A1 | 8/2018 | Freeman et al. | |
| 2019/0094552 A1* | 3/2019 | Shousha | G02B 27/0179 |
| 2021/0316660 A1* | 10/2021 | Kopp | G01S 15/931 |

\* cited by examiner

MEDICAL DEVICE FOR IMPROVING ENVIRONMENTAL PERCEPTION FOR BLIND OR VISUALLY-IMPAIRED USERS

FIELD

The invention relates to improving environmental perception, in particular for blind or visually-impaired users.

The term "blind users" is understood to mean persons afflicted by long-term blindness or blindness simply caused by circumstances, such as for example with a view to a haptic use (in total darkness for a military or other usage), or as a complement for virtual or augmented reality or other use.

BACKGROUND

Retinal implants are known from the prior art. These are devices surgically implanted at the back of one of the eyes of the blind person, electrically stimulating the neurons destined for the brain, by reproducing an image carried by radio from a video sensor installed on glasses. However, their costs and the complexity of their implementation limit their adoption.

In parallel with these devices, portable devices for blind persons are also known from the prior art that are capable of converting a video image acquired from an environment facing the subject into a "tactile image" reproduced on the skin or mucous membranes of the subject. The version currently in use comprises a frontal video camera connected to an electro-stimulation unit (of low intensity), in this case on the tongue of the user. Although this reproduction is rather basic, it is still usable by blind people.

One major drawback of these devices is that their performance is greatly reduced when the object targeted by the camera is mobile. Typically, the user has to turn their bust, their neck, their head, toward a direction of origin of a sound or other. Eventually, such a system finally tires out the user who gets fed up of the device.

SUMMARY

The present invention will improve the situation.

For this purpose, it provides a device offering an improvement in the spatial perception of an environment, by measuring the movements of the eyes of the blind subject and by closed-loop controlling, as a function of this measurement, the image that is reproduced on the skin.

Thus, the present invention is aimed at a device for improving environmental perception for blind or visually-impaired users, the device comprising:
at least one set of mechanical actuators intended to be in contact with the skin of a user,
at least one digital camera arranged for acquiring a current digital image of an environment facing the user,
a processing circuit connected to the camera for receiving signals from pixels of the acquired digital image and converting at least a part of the pixel signals into control signals each supplying one mechanical actuator from the set of actuators. In particular, the device furthermore comprises at least one eye-tracking module for at least one eye of the user so as to identify a direction of gaze of the user. Furthermore, the processing circuit is arranged for selecting, in the environment filmed by the camera, an area of acquired current image which depends on the direction of gaze, and for converting the signals from pixels of the aforementioned area into control signals each supplying an actuator of the set for stimulating the skin of the user.

The term "mechanical actuators" is understood typically to mean elements which may be arranged in a matrix for example, and each being capable of moving upon receipt of an electrical pulse. These may thus be piezoelectric elements designed for example to have:
a displacement with an amplitude that is a function of the electrical signal that they receive, and/or
a frequency of displacement that is a function of the electrical signal that they receive.

These may alternatively be or piezoelectric elements combined with systems of the micro-electro-mechanical (or "MEMS") type.

As a further variant, an emission of focused ultrasound waves distributed over a plane matrix may be used for stimulating the skin of the user. As yet another variant, an electrode may be provided emitting electrical pulses felt as mini-electric shocks (whose intensity may characterize an image gray level, and with a repetition frequency characterizing a particular color, as will be seen later on by way of exemplary embodiment).

"Skin" of the user hereinabove is understood to mean both the skin of the user (on the torso or elsewhere) and mucous membranes such as the palate, the tongue or other, which also corresponds to the generic medical term "integument". Thus, the actuators may take the form of electrodes addressing micro-currents, and accommodated for example in an intra-buccal false-palate (like the part bonded to the palate of a denture), which does not prevent the user from either talking, eating or drinking.

The term "digital camera" is furthermore understood to mean the fact that the image acquired of the environment comprises pixels typically arranged as a matrix, and an electrical signal may be assigned to each pixel for supplying an actuator. For example, for a monochrome ("Black and White") image, the intensity of the electrical signal supplying an actuator may be proportional to a gray level (from dark-black gray to light-white grey) of a pixel. Depending on the intensity of this electrical signal, the mechanical actuator may be displaced with a larger or smaller amplitude and/or frequency.

Thus, the device in the sense of the invention allows the attention of the user, focused on a particular area of the environment, to be reproduced by virtue of the eye-tracking measurement of the user and hence of their gaze. For example, if the user has heard a sound in a particular direction, they may direct their gaze toward this direction which the device realizes by then reproducing a "tactile image" of the area of the environment selected in this direction.

For this purpose, the invention has had to overcome a prejudice according to which blind people lose their eye-tracking faculty. However, for those who have recently become blind at least (and assuming that they have kept their eyeballs), counter-intuitively it has been observed that the eye movements of blind people are still present (despite their blindness).

Thus, the present invention is aimed at a device taking the form of a unit of equipment (or an apparatus) controlled by a software application and intended to be used for the purposes, notably, of reducing the effect of a handicap (in this case the blindness of a blind user). In this respect, the device of the invention may be considered as a medical device.

In one embodiment, the processing circuit may be arranged for selecting in an acquired current image a limited area of the current image which depends on the direction of gaze, and for converting the signals from pixels of said limited area into control signals each supplying one actuator from the set for stimulating the skin of the user.

In one variant, it may be arranged for the camera (not necessarily wide-angle) to be mobile in rotation in order to follow the direction of the gaze of the user. Nevertheless, it may be advantageous to implement a fixed (wide-angle) camera and to select by computer the relevant area in the image thus acquired in wide-angle according to the direction of the gaze.

It may however also be arranged for wide-angle cameras, which are also mobile in rotation (at least azimuthally), to track a movement of the eyes converging toward the nose of the user (which corresponds to a search for "near vision"). Furthermore, these cameras are able to autofocus (with a blur detection module), which allows the user to be offered a spatial perception of the environment, both in the nearby space ("near vision") and far away ("far vision"). Outside of the focusing situations and in particular for a "far vision", the cameras may be adjusted by default with an orientation relative to one another while complying as closely as possible with the physiological orientation of the homolateral eyes of the user (around 15° laterally with respect to the sagittal plane, being therefore around 30° for the orientation of one camera with respect to the other).

In one possible embodiment, the device furthermore comprises:
two sets of mechanical actuators intended to be in contact with the skin of a user, and
two eye-tracking modules for the respective eyes of the user, for defining two areas in the current image and converting the signals from pixels of each of the two areas into two respective sets of control signals supplying the two respective sets of actuators.

By applying an eye-tracking to each of the eyes of the user, the device can provide, by virtue furthermore of the pair of sets of mechanical actuators, a perception in three dimensions of the space in front of the gaze of the user. Indeed, thanks to this binocularity, both for the eye-tracking and for the sets of mechanical actuators, the device can provide the user with a perception in three dimensions of the space being looked at. As will be seen hereinbelow with reference to FIG. 1, the sets of actuators are distinct from one another and spatially separated, but the human brain is nevertheless naturally configured for reproducing a single, three-dimensional, image starting from two separate two-dimensional images (as it usually does with the two eyes of the user).

Thus, for a person who is blind but here assumed to still possess the faculty for moving their two eyes, the user can receive the two "tactile images" on their skin, which may be mutually confirmed for a 3D perception.

Nevertheless, this is a sophisticated embodiment. A single eye-tracking module may be provided (for reasons of economy or else if the user only has one eye whose pupillary movements may be measured), potentially with two cameras for filming the environment facing the user (potentially with an angle of around 30° between each camera axis so as to comply with the usual physiological orientation of the optical axes of the eyes). The only possible indeterminate by using a single eye-tracking is the discrimination:
of a situation where the user is looking at a near image, with a usual convergence of the eyes toward the nose, and
of a situation where the user is looking into the distance but to one side, and toward the nose.

In this case, the cameras may be "autofocus" and thus differentiate between each of these two situations.

In one embodiment of the invention, the camera and the eye-tracking module, at least, are mounted onto a common mechanical support, the eye-tracking module being oriented toward one eye of the user (typically the homolateral eye of the user), the camera being oriented for acquiring a current digital image of an environment facing the user. Thus, the camera may be oriented along the physiological axis of the homolateral eye of the user (or each camera oriented along the axis of one eye.

Thus, the distance between the camera and the eye-tracking module remains constant over time on the support, allowing the position of the gaze of the user to be correlated with what the camera is filming at any given time.

Advantageously, the camera is of the wide-angle type with a focal distance between 10 and 35 mm.

In one embodiment of the invention, the device comprises a wireless link for the transmission of the control signals to the actuators for at least one connection between the processing circuit and the actuators.

The wireless link offers the advantage of, for example, connecting the actuators (which may stimulate the torso or the back of the individual as described hereinbelow with reference to FIG. 1) to the rest of the device, in a compact manner, and for example creating a link between a mechanical support grouping the of eye-tracking modules, the cameras and the processing circuit, etc., with the mechanical actuators.

Since the skin of the hands of a user is particularly sensitive, in one variant, it may be provided for the mechanical actuators to be integrated into gloves, the sets of mechanical actuators being advantageously placed in the form of respective patches on the palm of the hands of the user, for example. A glove with a patch of mechanical actuators is for example provided for each hand, each of which corresponds to one image of the environment to be perceived (thus with a possible three-dimensional reconstruction). The cameras, eye-tracking modules and processing circuit may be mounted onto a common support and wirelessly connected to the patches of the gloves.

In one variant where the mechanical actuators may stimulate a part of the head of the user (for example the forehead as illustrated in FIG. 5), the assembly (camera, eye-tracking module, etc., together with the actuators) may be mounted onto a common support, for example in the form of a headset taking the forehead and coming down over the eyes of the user.

In one embodiment, the actuator is arranged for stimulating the skin of the user according to an intensity that is a function of the control signal received, and the control signals are each functions of an intensity of color of pixel.

"Intensity of color of pixel" is understood to mean a brightness of the pixel for a given color.

For example, for a "black and white" image, each actuator may be activated as a function of the gray level of the pixel going from white to black. As a variant, a set of three actuators may be provided for each pixel of a color image, each actuator having an intensity or a vibrational frequency that is a function of the level of "red, blue, green" color of this pixel.

For example, for the "reproduction" of a color image, it may be that the brightness of a pixel (from dark to light for example) is converted into intensity of actuator movement (thus pressing harder on the skin of the user), whereas the frequency of vibration of each actuator may be determined by the type of color (red or blue or green) assigned to this actuator. For example, the actuators reproducing the levels of blue vibrate faster than the actuators reproducing the level of red (green or yellow being represented by actuators having an intermediate frequency of vibration).

Thus, in an embodiment where each actuator is mobile in vibration for stimulating the skin of the user by cyclical vibrations, the frequency of the vibrations of an actuator may depend on a type of pixel color.

In one embodiment, the area of image may be of general shape corresponding to a shape of visual field of the eye tracked by the eye-tracking module, and the actuators of the set of actuators may then be disposed so as to be distributed according to a two-dimensional shape corresponding to this shape of visual field.

Thus, it will be understood that, in the device, a "one-to-one" correspondence is provided of a pixel of the area with an actuator of the set. A number of actuators of the set may thus be provided corresponding to the number of pixels in the area. Spatially, a correspondence of positions of the pixels in the area and respective actuators in the set of actuators may also be provided. Nevertheless, this is one exemplary embodiment. For example, an actuator may be associated with a group of four pixels of the image or more (with an average gray level for example). Similarly, the actuators may not be regularly spaced within the set of actuators (since the set of actuators may extend over more or less sensitive areas of the body, the more sensitive areas being typically able to receive more actuators).

The device may typically comprise a processing circuit notably for driving the actuators based on the pixels of the area of image acquired. This processing circuit then implements a method, subject furthermore of the present invention and comprising the steps:

receive signals from pixels of the acquired digital image,
receive a measurement by eye-tracking of a direction of gaze of the user,
determine a bounding in the acquired image of an area corresponding to the direction of the gaze, and select the signals from pixels of said area,
convert the signals from pixels of said area into control signals each intended to supply one actuator of the set of mechanical actuators, the number of pixels in said area corresponding to a number of actuators that the set of mechanical actuators comprises,
transmit the respective control signals to the actuators of said set.

The processing circuit of the device may typically comprise (as illustrated in FIG. 4) a processor and a memory storing the instructions of a computer program for the implementation of this method when these instructions are executed by the processor. The present invention is also aimed at such a computer program (whose general algorithm may be illustrated by FIG. 3 described hereinafter).

BRIEF DESCRIPTION OF THE DRAWINGS

Furthermore, other advantages and features of the invention will become apparent upon reading the description of exemplary embodiments presented hereinafter, and upon examining the appended drawings, in which.

DETAILED DESCRIPTION

Figure 1:
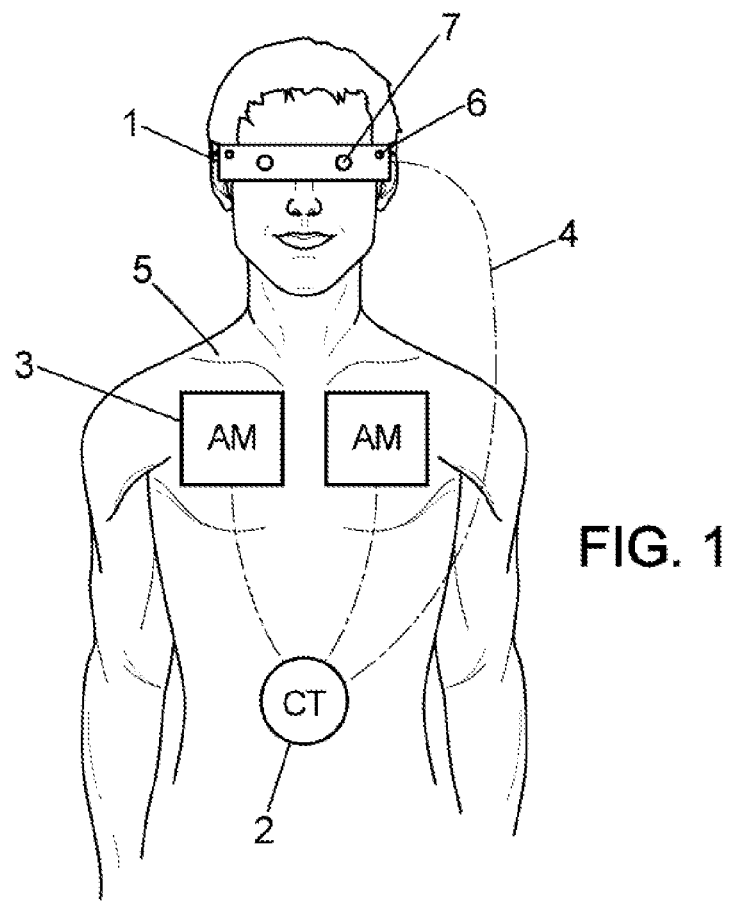
FIG. 1 shows an individual wearing a medical device for improving environmental perception, subject of the invention, according to a first exemplary embodiment.

FIG. 1 shows a device for improving environmental perception typically in the space in front of a user. The device is worn by a blind or partially-sighted user 5, this device comprising a mechanical support 1 integrating a wide-angle camera 6 and an eye-tracking module 7. More precisely, in the case where the eyes of the user are both still moving and when an eye-tracking is then possible on each eye, the device may comprise, as illustrated in FIG. 1, two wide-angle cameras 6, each for filming the environment in front of each eye of the user, and two eye-tracking modules 7, each for tracking the movements of one eye.

Typically, the two cameras, notably wide-angle, are installed in fixed respective positions on the support 1, and the areas selected in the wide-angle images partially overlap in order to provide a stereoscopic effect, allowing a 3D perception. For this purpose, the device furthermore comprises two sets of mechanical actuators 3 spatially separated as illustrated in FIG. 1.

The cameras 6 and tracking modules 7 are connected via wired link to a processing circuit 2 driving the two sets of mechanical actuators 3.

In the example shown, the mechanical support 1 is placed on the head of the user 5, whereas the two sets of mechanical actuators 3 are positioned on the torso of the user 5. The movements of the eyes of the user 5 are measured by means of the eye-tracking modules 7 in real time. Furthermore, here by way of example, an area in the acquired images is selected which corresponds to the current direction of the gaze of the user. Alternatively, cameras (not necessarily wide-angle) may be mounted on respective pivoting axes and the cameras oriented in the direction of the current gaze of the user. In yet another alternative, a single wide-angle camera may be provided but with an eye-tracking for each eye, and two areas selected in the environment filmed, the stereoscopic effect being again provided by a partial overlap of these two areas.

In the embodiment where the environment is filmed by one or more cameras of the "wide-angle" type, the focal distance of such cameras is chosen so as to cover in the acquired images what the visual field of the user 5 would correspond to if they were able-bodied.

Figure 6:
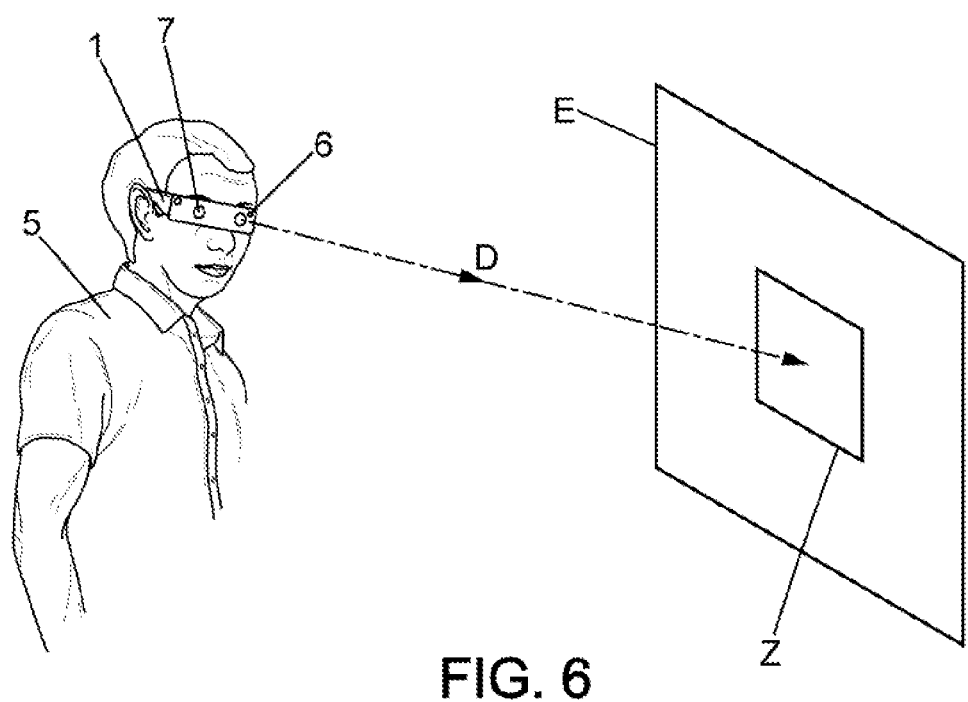
FIG. 6 shows an individual 5, wearer of a device in the sense of the invention, observing an environment facing them.

The movements of the eyes of the user 5 are measured simultaneously with the shooting of the environment by the wide-angle cameras 6. More precisely, as illustrated in FIG. 6, the measurements carried out by the eye-tracking modules 7 are analyzed by the processing circuit 2 in order to select, according to the measurement of the direction D of the gaze (for each eye), the appropriate area Z of pixels of the current image of the environment E which has just been acquired by the wide-angle camera 6.

The measurements carried out may be sent to the processing circuit 2 by means of a wireless link. Indeed, a wireless link in this application allows less restriction and a greater freedom of movement for the user 5, the processing circuit 2 and the mechanical actuators 3 being located on the torso (or the back typically) of the user 5.

The processing circuit 2 processes the received data and sends the instructions to the mechanical actuators AM of the sets 3.

The mechanical actuators 3 positioned on the bust stimulate the skin of the user 5 according to the instructions received by the processing circuit 2. They "reproduce" on the skin the images modified after the processing of the data in the processing circuit 2.

In practice, the processing circuit 2 converts a pixel intensity (gray level for example) for each pixel into a mechanical intensity of stimulation by an actuator. A particular frequency of vibration may be associated with each color of pixel (for example a low frequency for red and a higher frequency for blue). For example, an increasing frequency of vibration may also be assigned to the various colors from red to violet, in the colors of the visible spectrum.

Figure 2:
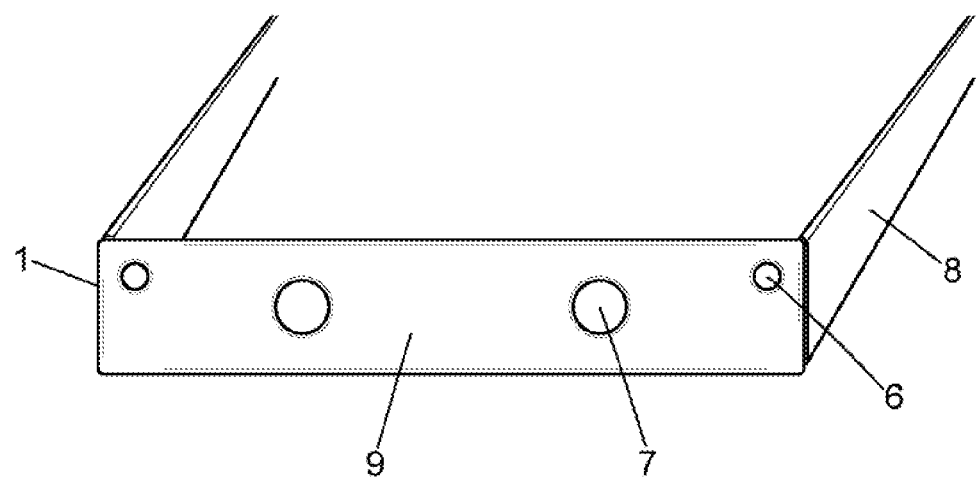
FIG. 2 is a perspective view of a part of the device subject of the invention with reference to FIG. 1.

FIG. 2 shows a perspective view of the mechanical support 1, with a face 9 and two branches 8 held on the face 9, for example mechanically rigidly attached to the latter via a hinged link (not shown). Two eye-tracking modules 7 are situated toward the eyes typically for filming the pupils and tracking their movements (often by shape recognition implemented by a computer module in the images thus acquired) and, from there, determining a direction of the gaze of the user. On the other hand, the two wide-angle cameras 7 are positioned in the direction of the environment (along the physiological axes of the eyes of the subject).

Figure 3:
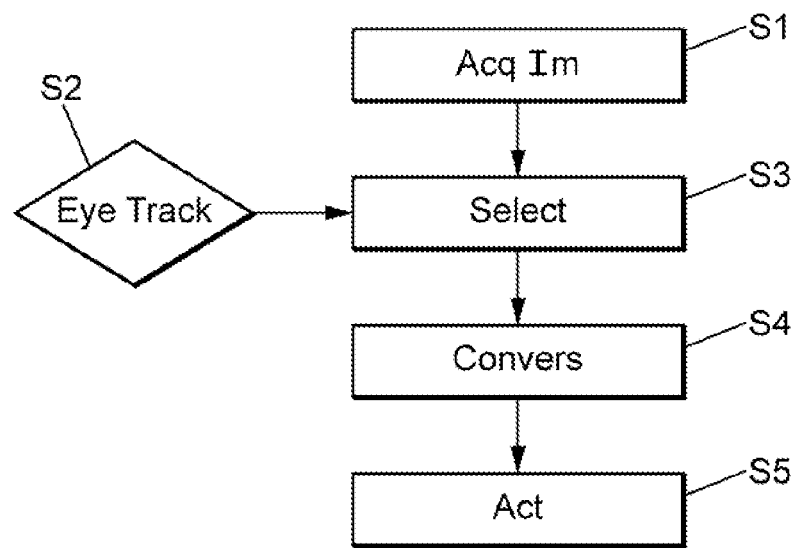
FIG. 3 corresponds to a flow diagram of the general algorithm of the method subject of the invention with reference to FIG. 1.
Figure 7:
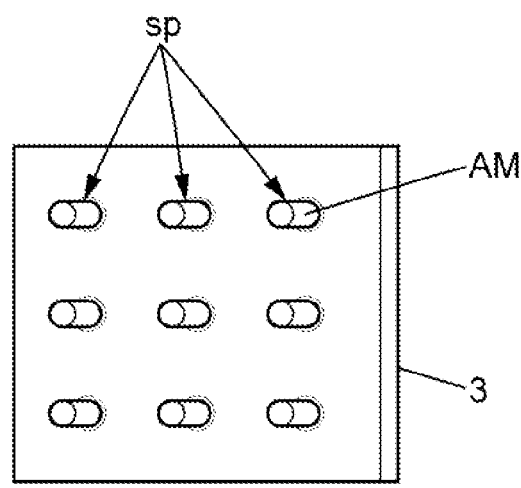
FIG. 7 illustrates schematically one of the sets of mechanical actuators.

FIG. 3 shows a flow diagram summarizing possible steps of a method implemented by the processing circuit 2. Such a method may comprise, at the step 51, the acquisition of a current image by a camera 6. At the step S2, an eye-tracking is implemented in order to determine a current direction of the gaze of the user (based on measurements by eye-tracking of the direction of gaze of the user 5 by the eye-tracking module or modules 7). The visual field is thus made coherent with the orientation of the gaze. At the step S3, depending on this current direction of the gaze, an area Z corresponding to the direction of the gaze D is selected in the acquired image of the environment E (as described hereinabove with reference to FIG. 6). More particularly, the signals from pixels of this area Z are selected for converting them, at the step S4, into control signals sp for the mechanical actuators AM (sets of actuators 3 such as illustrated in FIG. 7). These may be piezoelectric elements or MEMS as described hereinabove, controlled by electrical signals sp with a view to driving these elements in vibration:

At an amplitude of vibration that is a function of the pixel intensity (gray level, for example), and
At a frequency of vibration being determined by the type of color (with three frequency levels for blue, green or red for example).

At the step S5, these control signals are subsequently sent to the mechanical actuators AM.

It goes without saying that these steps S1 to S5 are carried out for each eye (and hence each current camera image), and successively for all the images successively acquired, in real time.

The two vibrational images of the two mechanical actuators 3 on the skin are intended to be as close as possible to those that the retinas would have captured if the subject had been able-bodied. Such an embodiment allows the surrounding space to be re-taught to the individual 5.

Figure 4:
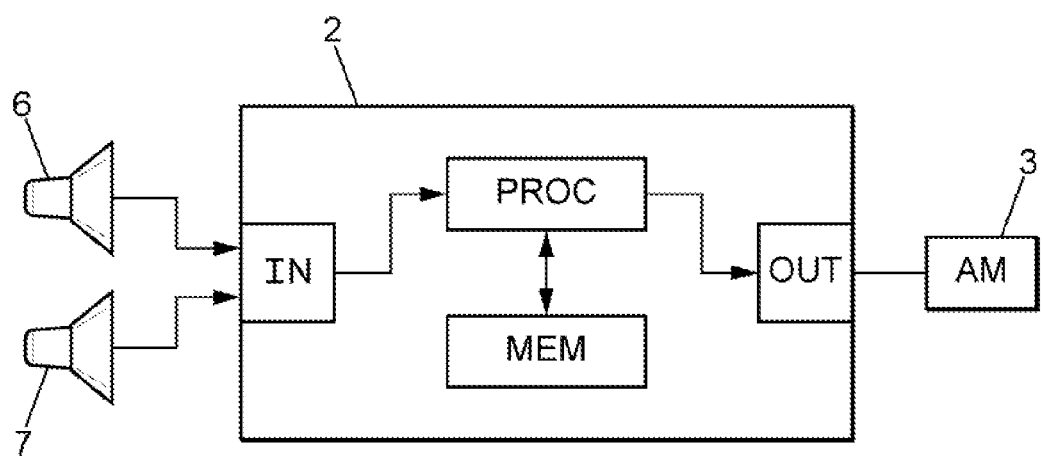
FIG. 4 illustrates schematically a processing circuit notably of the device shown in FIG. 1.

FIG. 4 shows the device in a schematic form comprising the wide-angle cameras 6 and the eye-tracking modules 7, together with the processing circuit 2 here comprising:
an input interface IN for receiving the signals from the equipment 6 (pixels of current image) and 7 (measurement of direction of the gaze),
a memory MEM for storing, at least temporarily, data corresponding to these signals, together with instructions of a computer program in the sense of the invention, for the implementation of the method described hereinabove with reference to FIG. 3,
a processor PROC capable of cooperating with the input interface IN and with the memory MEM for reading and executing the instructions of the computer program and thus delivering control signals for the actuators AM, via
an output interface OUT connected to the sets of actuators 3.

Figure 5:
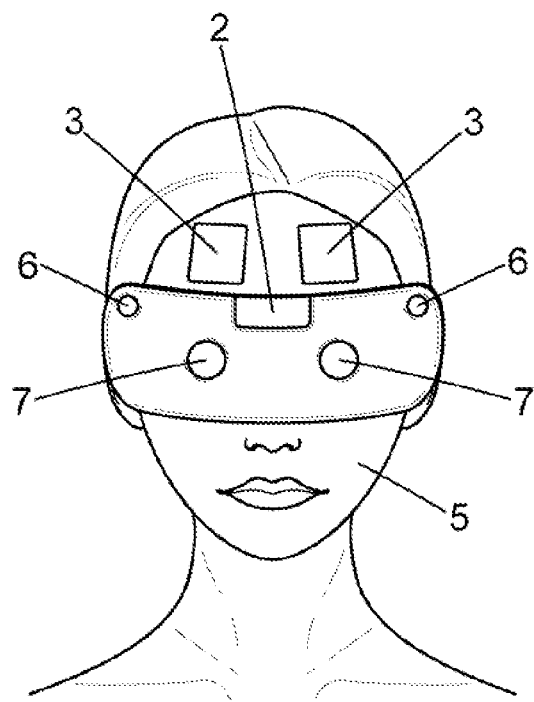
FIG. 5 shows an individual wearing a medical device for improving environmental perception, according to a second exemplary embodiment.

FIG. 5 shows a device for improving the spatial perception of an environment, worn by a user 5 on the head. The device comprises a mechanical support 1 extending on either side of the head and two mechanical actuators 3 positioned on the forehead of the individual 5. The mechanical support 1 comprises a face 9 and two branches 8 held on the face as illustrated in FIG. 2. In contrast to the device illustrated in FIG. 1, the processing circuit 2 is integrated into the mechanical support 1. The mechanical support 1 takes the form of a headset allowing complete freedom for the user 5. Here, a short wired link between the mechanical support 1 and the mechanical actuators 3 may be provided in this embodiment. This is because it does not limit the user 5 in their movements and the entire device is on the head of the user.

It goes without saying that the present invention is not limited to the exemplary embodiments described hereinabove, and it may be extended to other variants.

Thus, for example, a frequency of vibration specific to a color has been described hereinabove. As a variant, for a black and white image, a frequency of vibration may be chosen that varies as a function of the gray level of each pixel.

Previously, a distribution of the actuators of the set of actuators has been defined according to a two-dimensional shape corresponding to the shape of visual field that the selected area of image takes, with in particular a number of actuators in each set corresponding to the number of pixels in the selected area of image. Nevertheless, as a variant, it is possible to progressively render actuators of the set active in increasing number (starting from the center of the set of actuators up to the entirety of the actuators of the set) as the user becomes accustomed to the device. As yet another a variant, it is possible to average the amplitudes of vibration (or other stimuli) of n actuators from amongst the N actuators of the set, then to subsequently refine the definition of perception by making n decrease, again as the user gets accustomed to the device. It goes without saying that, in order to expedite this adaptation, it is also possible to correct (by computer) and thus reduce initial oculomotor aberrations, in order to attenuate saccadic eye movements for example.

The invention claimed is:

1. A device for improving environmental perception for blind or visually-impaired users, the device comprising:
at least one set of mechanical actuators intended to be in contact with the skin of a user, at least one digital camera arranged for acquiring a current digital image of an environment facing the user, a processing circuit connected to the camera for receiving signals from pixels of the acquired digital image and converting at least a part of the pixel signals into control signals each supplying a mechanical actuator of the set of actuators, wherein the device furthermore comprises at least one eye-tracking module for at least one eye of the user for identifying a direction of gaze of the user, wherein the processing circuit is arranged for selecting in the environment filmed by the camera an area of acquired current image which depends on the direction of gaze, and converting the signals from pixels of said area into control signals each supplying an actuator of the set for stimulating the skin of the user, and wherein the processing circuit is further arranged for selecting within an acquired current image a limited area of the current image which depends on the direction of gaze, and converting the signals from pixels of said limited area into control signals each supplying an actuator of the set for stimulating the skin of the user.

2. The device as claimed claim 1, comprising:

two sets of mechanical actuators intended to be in contact with the skin of a user, and two eye-tracking modules for the respective eyes of the user, for defining two areas in the current image and converting the signals from pixels of each of the two areas into two respective sets of control signals supplying the two respective sets of actuators.

3. The device as claimed in claim 1, wherein the camera and the eye-tracking module, at least, are mounted onto a common mechanical support, the eye-tracking module being oriented toward one eye of the user, the camera being oriented so as to acquire a current digital image of an environment facing the user.

4. The device as claimed in claim 1, wherein at least one connection between the processing circuit and the actuators is a wireless link for the transmission of the control signals for the actuators.

5. The device as claimed in claim 1, wherein each actuator is arranged for stimulating the skin of the user according to an intensity that is a function of the control signal received, and the control signals are each functions of an intensity of color of pixel.

6. The device as claimed in claim 5, wherein each actuator is mobile in vibration for stimulating the skin of the user by cyclical vibrations, the frequency of the vibrations of an actuator being determined by a type of color of pixel.

7. The device as claimed in claim 1, wherein the image area is of general shape corresponding to a shape of visual field of the eye tracked by the eye-tracking module, and the actuators of the set of actuators are distributed according to a two-dimensional shape corresponding to said shape of visual field.

8. A method implemented by a processing circuit of a device as claimed in claim 1, wherein the method comprises:

receive signals from pixels of the acquired digital image, receive a measurement by eye-tracking of a direction of gaze of the user, determine a bounding in the acquired image of an area corresponding to the direction of the gaze, and select the signals from pixels of said area, convert the signals from pixels of said area into control signals each intended to supply one actuator of the set of mechanical actuators, the number of pixels in said area corresponding to a number of actuators that the set of mechanical actuators comprises, transmit the respective control signals to the actuators of said set.

9. A non-transitory computer storage, storing instructions of a computer program causing the implementation of the method as claimed in claim 8, when said instructions are executed by a processing circuit of a device for improving environmental perception.

* * * * *